United States Patent [19]

Casnati et al.

[11] 4,151,201
[45] Apr. 24, 1979

[54] PROCESS FOR PREPARING 2-HYDROXYBENZOIC ALDEHYDES

[75] Inventors: Giuseppe Casnati; Giovanni Casiraghi, both of Parma; Giuseppe Puglia, Reggio Emilia; Giovanni Sartori, Vicobellignano; Giuliana Terenghi, Parma, all of Italy

[73] Assignee: Montedison S.p.A., Milan, Italy

[21] Appl. No.: 824,090

[22] Filed: Aug. 12, 1977

[30] Foreign Application Priority Data

Aug. 13, 1976 [IT] Italy ............................ 26270 A/76

[51] Int. Cl.² .......................................... C07C 45/00
[52] U.S. Cl. ............................ 260/562 A; 260/600 R
[58] Field of Search .............. 260/600, 562 A, 600 R

[56] References Cited

U.S. PATENT DOCUMENTS

| | | | |
|---|---|---|---|
| 2,903,483 | 9/1959 | Berres | 260/600 |
| 3,173,956 | 3/1965 | Grinstead | 260/600 |
| 3,271,412 | 9/1966 | Raue et al. | 260/600 X |
| 3,349,115 | 10/1967 | Weil et al. | 260/600 X |
| 3,833,660 | 9/1974 | Smith | 260/600 X |
| 3,838,173 | 9/1974 | Royer et al. | 260/600 X |

*Primary Examiner*—Bernard Helfin

[57] ABSTRACT

There is disclosed a catalytic process for preparing, from phenols and formaldehyde 2-hydroxybenzoic aldehydes some of which are new in the art and, more particularly, a high-selectivity process for preparing the aldehydes by direct synthesis from phenols having at least a free ortho position and formaldehyde, in the presence of a catalyst consisting of anhydrous stannous and/or stannic chloride and of an aprotic binder.

8 Claims, No Drawings

PROCESS FOR PREPARING 2-HYDROXYBENZOIC ALDEHYDES

THE PRIOR ART

Known processes for the synthesis of salicylic aldehydes can be summarized as follows:

(a) direct or indirect non-selective processes which result in more or less complex mixtures and present the implicit and serious drawback of separating the salicylic aldehydes from the complex mixture and then purifying the aldehydes, the negative consequences of which are the low total yield of the aldehydes and, particularly for the indirect processes, the labor and economic burden involved. Of the several such processes available, the best known is the Reimer-Tremann synthesis, and modifications thereof, according to which a phenol is reacted with chloroform under alkaline conditions and resulting in a variable mixture of ortho and para hydroxy-benzaldehydes;

(b) indirect selective processes which, although leading to a single product in generally easily separable from the reaction mass, nevertheless have the disadvantage of either comprising two or more steps with optional isolation of intermediate products or of starting with a substance other than a phenol which, in its turn may have to be synthesized under particular conditions, thus substantially reducing the actual commercial practicality of the process. Processes of this type (b), also those of industrial interest, include the synthesis of salicylic aldehydes by oxidation of the corresponding alcohols which, in turn, are generally prepared from phenols and formaldehyde under appropriate conditions, and the Raschig process involving the chlorination of esters of ortho cresol at high temperatures, successive hydrolysis of the chlorinated product, etc.

Direct catalytic selective processes, to which type the process of this invention belongs, are those which use, directly and as a starting substrate, a phenol which is generally readily available and which comprise one step only, without isolation of intermediate products of any kind.

The known processes of the last-mentioned type, being in principle of the utmost interest from the industrial viewpoint, are very few. One such industrial process comprises reacting phenols and carbon monoxide in the presence of considerable amounts of aluminum phenoxides and under rather severe conditions, e.g., at a temperature of 100°–350° C. and a pressure of 1 to 300 atmospheres. However, this process has the serious drawback of having to operate with carbon monoxide under pressure and of utilizing rather large amounts of the particular catalyst (aluminum phenoxide) and of being, therefore, economically burdensome.

THE PRESENT INVENTION

One object of this invention is to provide a simple, economical, highly selective method of preparing salicylic aldehydes in good yields, operating at relatively moderate temperatures and at atmospheric pressure, and employing small amounts of a relatively inexpensive and readily available catalyst, which features distinguish said method over any of the known processes and render it superior thereto.

Said object, and other objects which will more clearly appear to those skilled in the art hereinafter, are accomplished by this invention in accordance with which 2-hydroxybenzoic or salicylic aldehydes of formula (I)

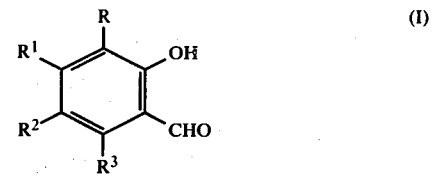

wherein R, $R^1$, $R^2$ and $R^3$, which may be the same or different, represent a hydrogen atom; an alkyl, aryl or cycloalkyl group; an alkoxyl, hydroxyl or acylamino group; or halogen are prepared by condensing a phenol of general formula (II)

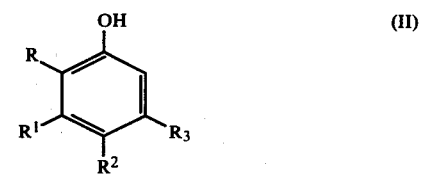

wherein R, $R^1$, $R^2$ and $R^3$ have the same meaning as in general formula (I), with formaldehyde at temperatures of from about 90° C. to 150° C., preferably at about 110° C., in a substantially stoichiometric molar ratio of phenol to formaldehyde, in the presence of anhydrous stannous and/or stannic chloride in amounts of from about 0.02 to 0.2 mole, preferably about 0.1 mole, of Sn per mole of phenol used, and of at least one binder selected from the group consisting of pyridine, alkylpyridines, acetylpyridines, hexamethylphosphotriamide, tetramethylethylene diamine, tetramethylpropylene diamine, quinolines, quinoxalines, anilines, substituted anilines, and tertiary amines, in an amount of from about 0.1 to 0.6, preferably about 0.4, mole per mole of phenol used, and in an aprotic solvent such as toluene, xylenes, cumene, alkylbenzenes, decalin and anisole, the concentrations not being critical and concentrations of from 20% to 50% by weight being useful.

By the process of this invention it is possible to obtain a direct, selective synthesis of the 2-hydroxybenzoic or salicylic aldehydes through an exclusive linking of formaldehyde only to carbon in ortho position with respect to the hydroxyl group of the starting phenol, independently of whether the para position is free or carries a substituent.

As disclosed hereinabove, the starting phenol (II) may be substituted by radicals containing a variable, even a high, number of carbon atoms, the number of carbon atoms in the substituents not being critical for the purposes of this invention.

As also disclosed hereinabove, the catalyst used in the present process is anhydrous stannous and/or stannic chloride. In a presently preferred embodiment it is anhydrous $SnCl_2$.

Not only formaldehyde as such, but also industrial formaldehyde, i.e., in practice paraformaldehyde, can be used in the present process.

The phenol/formaldehyde molar ratio is practically stoichiometric, variations in excess being allowable as a function of the titer of the formaldehyde available.

The presently peferred catalyst, anhydrous $SnCl_2$, can be prepared by conventional methods, e.g., by dehydration with acetic anhydride of commercial dihydrated stannous chloride (see H. Stephen, J. Chem. Soc. 2786 (1930).

In the practice of the present process, reaction times can vary depending on the temperature, the particular starting phenol, etc. In general, and in practice, the reaction time is from 3 to 10 hours. For best results, the reaction is carried out with stirring of the reactants.

In accordance with a presently preferred embodiment of the invention, the phenol and paraformaldehyde, in stoichiometric ratio, are introduced into a reactor made of pyrexglass, stainless steel, or other suitable material and equipped with a thermometer, a stirrer and a proportioning system for the reactants, after which the catalyst (anhydrous stannous chloride), and the binder (pyridine) are added in the predetermined amounts, followed by the addition of the solvent. The reacting mass is then heated for about 8 hours up to a temperature of about 110° C.

After cooling, the mass is filtered and subjected to distillation in a steam flow. The distillate contains exclusively the desired salicylic aldehyde, variable amounts of unreacted starting phenol and methanol.

Separation and purification of the salicylaldehyde from the distillate are effected by conventional methods either by fractional distillation, optionally at reduced pressure, or by crystallization in the case of difficultly distillable aldehydes.

The present one-step process is particularly advantageous due to the simplicity of the operating conditions. The most significant advantage is the surprising regionselectivity of the formaldehyde linking to the phenol only to carbon in ortho position respect to the hydroxyl group, with good yields, a high selectivity, and practically without the formation of resinous by-products and/or of polycondensation by-products.

The following Examples 1 to 17 are given to illustrate the invention in more detail and are not intended to be limiting.

The parameters of the exemplified syntheses including conversions, yields and selectivities are reported in Tables I-IV, other data being specified in the individual examples.

Table V reports, for comparative purposes, the syntheses conducted in Example 18 under conditions not corresponding to those characterizing the present invention; in these cases it is stressed that no acceptable results are obtained. Finally, the aldehydes prepared in Examples 3, 5, 7, 8, 10, 12 and 14 are new products in the art.

The formaldehyde used in the examples had a titer varying from 80% to 95%, in such cases the phenol (II): raw formaldehyde ratio reached values equal to 1:3.

EXAMPLE 1

2-hydroxybenzaldehyde (salicylic aldehyde)

(a) Use of anhydrous $SnCl_2$.

9.4 g (0.1 mole) of phenol, 9 g (0.3 mole) of the paraformaldehyde, 1.9 g (0.01 mole) of anhydrous stannous chloride and 3.72 g (0.04 mole) of 4-picoline in 200 cc of toluene were introduced into a pyrex glass reactor equipped with a thermometer, a stirrer and a reflux cooler, and were heated under stirring for 8 hours up to 110° C.

After cooling, the reaction mass was filtered and subjected to distillation in a steam flow.

The distillate was repeatedly extracted with ether, and the extracts were dried on anhydrous $Na_2SO_4$. Ether was finally evaporated and the residue was subjected to fractional distillation under the vacuum created by a water pump (about 16 mm/Hg), the fraction passing between 85° and 90° C. being collected.

7.2 g (yield calculated on the theoretical value=59%) of a product boiling at 197° C. were thus obtained.

(b) Use of anhydrous $SnCl_4$.

By operating as in (a) but substituting 2.6 g of anhydrous $SnCl_4$ for $SnCl_2$, 3.1 g (yield calculated on the theoretical value=26%) of the same product were obtained.

The centesimal, infrared and nuclear magnetic resonance analyses were in agreement with the formula $C_7H_6O_2$.

EXAMPLE 2

2-hydroxy-3-methylbenzaldehyde (a) Use of anhydrous $SnCl_2$.

By following modalities similar to those of Example 1 and using 10.8 g (0.1 mole) of ortho-cresol, 11.5 g (yield calculated on the theoretical value=85%) of a product having a boiling point of 208°-209° C., distilled between 100° and 105° C. at 16 mm/Hg, were obtained.

(b) Use of anhydrous $SnCl_4$.

By operating as in case (a) and substituting 2.6 g of anhydrous $SnCl_4$ for $SnCl_2$, 6.8 g (yield calculated on the theoretical value=50%) of the same product were obtained. The centesimal, infrared, nuclear magnetic resonance analyses were in agreement with the structure $C_8H_8O_2$.

EXAMPLE 3

2-hydroxy-3-tert.butylbenzaldehyde

By following a method similar to that of Example 1 and using 15 g (0.1 mole) of 2-tert.butyl phenol, 13.3 g (yield on the theoretical value=75%) of a product having its boiling point at 248° C., distilled between 125° and 130° C. at 16 mm/Hg, were obtained.

The centesimal analysis gave the following results: for $C_{11}H_{14}O_2$—calculated: C%, 74.13; H%, 7.92. Found: C%, 74.42; H%, 8.13.

The spectroscopic, infrared, ultraviolet, nuclear magnetic resonance and mass analyses were in agreement with the proposed structure, $C_{11}H_{14}O_2$.

EXAMPLE 4

2-hydroxy-3-tert.butyl-5-methylbenzaldehyde

By operating according to Example 1 but using 16.4 g (0.1 mole) of 2-tert.butyl-4-methylphenol, 18.2 g (yield calculated on the theoretical value=95%) of a product having a melting point at 73°-74° C. and a boiling point at 265°-267° C., distilled between 128° and 130° C. at 16 mm/Hg, were obtained.

The centesimal analysis gave the following results: for $C_{12}H_{16}O_2$—calculated: C%, 74.97; H%, 8.39. Found: C%, 74.81; H%, 8.43.

The structure was also confirmed by the spectroscopic, infrared, ultraviolet and nuclear magnetic resonance and mass analyses.

EXAMPLE 5

2-hydroxy-3,5-ditert.butylbenzaldehyde

By operating according to Example 1 and using 20.6 g (0.1 mole) of 2,4-ditert.butylphenol, 17.3 g (yield calculated on the theoretical value=74%) of a product having a boiling point at 290°-292° C., a melting point at 59°–60° C., distilled between 153° and 160° C. at 16 mm/Hg, were obtained.

The centesimal analysis gave the following results: for $C_{15}H_{22}O_2$—calculated: C%, 76.88; H%, 9.46. Found: C%, 77.12; H%, 9.45.

The spectroscopic, infrared, ultraviolet and nuclear magnetic resonance and mass analyses were in agreement with the structure, $C_{15}H_{22}O_2$.

EXAMPLE 6

2-hydroxy-3-isopropyl-6-methylbenzaldehyde

By operating according to Example 1 and using 15 g (0.1 mole) of thymol, 13.3 g (yield calculated on the theoretical value=75%) of a product having a boiling point at 261° C., distilled between 125° and 130° C. at 16 mm/Hg, were obtained.

The centesimal, infrared, ultraviolet and nuclear magnetic resonance analyses were in agreement with structure: $C_{11}H_{14}O_2$.

EXAMPLE 7

2-hydroxy-3-cyclohexylbenzaldehyde

Example 1 was repeated, but using 17.2 g (0.1 mole) of 2-cyclohexylphenol, 16.8 g (yield calculated on the theoretical value=84%) of a product having a melting point at 47°–48° C., a boiling point at 300°–302° C., distilled between 145° and 150° C. at 16 mm/Hg, were obtained.

The centesimal analysis gave the following results: for $C_{13}H_{16}O_2$—calculated: C%, 76.44; H%, 7.90. Found: C%, 76.31; H%, 8.11, said structure being confirmed, also, by the spectroscopic, infrared, ultraviolet, mass and nuclear magnetic resonance analyses.

EXAMPLE 8

2-hydroxy-4-tert.butylbenzaldehyde

By operating as in Example 1 and using 15 g (0.1 mole) of 3-tert.butylphenol, 12.8 g (yield calculated on the theoretical value=72%) of a product having a boiling point at 258°–260° C., distilled between 120° and 125° C. at 16 mm/Hg, were obtained.

The centesimal analysis gave the following results: for $C_{11}H_{14}O_2$—calculated: C%, 74.13; H%, 7.92. Found: C%, 74.46; H%, 7.81.

The spectroscopic, infrared, ultraviolet, mass and nuclear magnetic resonance analyses were also in agreement with the proposed structure: $C_{11}H_{14}O_2$.

EXAMPLE 9

2-hydroxy-4-chlorobenzaldehyde and 2-hydroxy-6-chlorobenzaldehyde

By operating according to Example 1 and starting from 12.8 g (0.1 mole) of 3-chlorophenol, 8.5 g of a mixture of both isomeric 2-hydroxy-chlorobenzaldehydes were obtained: distillation fraction passing between 125° and 130° C. at 16/mm Hg (total yield calculated on the theoretical value=55%). The separation of the two isomeric aldehydes was effected by chromatographic analysis on a silica gel by eluting with a mixture of hexane and ethyl acetate in a 9:1 ratio; 6.0 g of 2-hydroxy-4-chlorobenzaldehyde having a melting point at 51°–52° C. and a boiling point at 230° C., as well as 2.0 g of 2-hydroxy-6-chlorobenzaldehyde, having a melting point at 54°–55° C., were thus obtained.

The centesimal, infrared and nuclear magnetic resonance analyses agreed with the structure $C_7H_5O_2Cl$.

EXAMPLE 10

2-hydroxy-3-phenylbenzaldehyde

By operating according to Example 1 and starting from 17 g (0.1 mole) of 2-phenylphenol, 11.9 g of a product having a melting point at 47°–48° C. and a boiling point at 330°–335° C., distilled between 165° and 170° C. at 16 mm/Hg, were obtained.

The centesimal analysis gave the following results: for $C_{13}H_{10}O_2$—calculated: C%, 78.77; H%, 5.09. Found: C%, 78.43; H%, 5.40.

The spectroscopic, infrared, ultraviolet, mass and nuclear magnetic resonance analyses were in agreement with the proposed structure.

EXAMPLE 11

2-hydroxy-5-methoxybenzaldehyde

By operating according to Example 1 and starting from 12.4 g (0.1 mole) of 4-methoxyphenol, 6.8 g of a product having a boiling point at 247°–248° C., distilled between 115° and 120° C. at 16 mm/Hg, were obtained.

The centesimal, infrared and nuclear magnetic resonance analyses agreed with the structure: $C_8H_8O_3$.

EXAMPLE 12

2-hydroxy-3-nonylbenzaldehyde

By operating according to Example 1 and starting from 22.0 g of 2-nonylphenol, 16.1 g of a product (yield calculated on the theoretical value=65%) having a boiling point at 320° C., distilled between 168° C. and 175° C. at 16 mm/Hg, were obtained.

The centesimal analysis gave the following results: for $C_{16}H_{24}O_2$—calculated: C%, 77.37; H%, 9.74. Found: C%, 77.06; H%, 9.45.

The spectroscopic, infrared, ultraviolet, nuclear magnetic resonance and mass analyses agreed with the proposed structure.

EXAMPLE 13

2,5-dihydroxybenzaldehyde

The reaction was initially conducted as in Example 1, employing 11.0 g of hydroquinone. At the conclusion of the reaction the mass was filtered, repeatedly washed with water, dried on anhydrous $Na_2SO_4$ and finally evaporated to dryness. Aldehyde was separated from the solid residue by repeatedly crystallizing from a 1:1 benzene:petroleum ether mixture.

6.6 g (yield calculated on the theoretical value=48%) of a product having a melting point of 99° C. were obtained. The centesimal, infrared and nuclear magnetic resonance analyses agreed with the structure: $C_7H_6O_3$.

EXAMPLE 14

2-hydroxy-4-acetylaminobenzaldehyde

By operating according to Example 13, but using anisole as the solvent and a temperature of 100° C., and starting from 15.1 g of 3-acetylaminophenol, 9.0 g of a product (yield on the theoretical value=50%) having a melting point at 185°–186° C. were obtained.

The centesimal analysis gave the following results: for $C_9H_9O_3N$—calculated: C%=60.33; H%=5.06. Found: C%=60.60; H%=5.33. furthermore the spectroscopic, infrared, ultraviolet, nuclear magnetic resonance and mass analyses confirmed the structure.

EXAMPLE 15 (a–c)

By operating according to Example 2, condensations were conducted between ortho-cresol and formaldehyde in the presence of anhydrous $SnCl_2$ and 4-picoline in toluene under general condensation conditions variable in respect to those described in Example 2.

Condensation tests were conducted employing temperatures and ortho-cresol/formaldehyde ratios different from those of Example 2. Using operating conditions identical with that of Example 2, the results (conversions, 2-hydroxy-3-methylbenzoic aldehyde yields and selectivity) as reported in Table II were obtained.

EXAMPLE 16 (a–d)

Operating according to Example 2, condensations were conducted between ortho-cresol and formaldehyde in the presence of anhydrous $SnCl_2$ and 4-picoline in toluene under general condensation conditions variable in respect to those described in Example 2.

Condensation tests were conducted employing orthocresol/$SnCl_2$ ratios and ortho-cresol/4-picoline ratios different from those of Example 2.

Using operating conditions identical with those of Example 2, the results (conversions 2-hydroxy-3-methylbenzoic aldehyde yields and selectivity) reported in Table III were obtained.

EXAMPLE 17 (a–g)

Condensation between ortho-cresol and formaldehyde in the presence of anhydrous $SnCl_2$ in toluene, in the presence of various binders.

The results obtained by using operating conditions similar to those of Example 2, are reported in Table IV.

EXAMPLE 18 (a–q) (comparative test)

Condensation between ortho-cresol and formaldehyde under general condensation conditions different from those in practicing the present process.

By operating according to Example 2, condensation tests were conducted under conditions different from those of the present process with respect to temperature, nature and amount of the catalyst, nature and amount of the binder, and amount of the formaldehyde employed. The results obtained are reported in Table V.

TABLE I

Syntheses of salicylic aldehydes from phenols (0.1 mole) and paraformaldehyde (0.3 mole) in the presence of $SnCl_2$ (0.01 mole) and 4-methylpyridine (0.04 mole) in toluene (200 cc) at 110° C. for 8 hours. (The corresponding values obtained with a catalyst based on $SnCl_4$ are indicated between brackets).

| Ex. | Starting Phenol | Compound | Conv. % | Yield % | Selec. % |
|---|---|---|---|---|---|
| 1 | phenol | 2-hydroxybenzaldehyde | 68 (45) | 59 (26) | 86 (57) |
| 2 | o-cresol | 2-hydroxy-3-methylbenzaldehyde | 90 (70) | 85 (50) | 94 (71) |
| 3 | 2-tert . butylphenol | 2-hydroxy-3-tert . butylbenzaldehyde | 80 | 75 | 93 |
| 4 | 2-tert . butyl-4-methylphenol | 2-hydroxy-3-tert . butyl-5-methylbenzaldehyde | 100 | 95 | 95 |
| 5 | 2,4-ditert . butylphenol | 2-hydroxy-3,5-ditert . butylbenzaldehyde | 78 | 74 | 95 |
| 6 | thymol | 2-hydroxy-3-isopropyl-6-methylbenzaldehyde | 88 | 75 | 85 |
| 7 | 2-cyclohexylphenol | 2-hydroxy-3-cyclohexylbenzaldehyde | 90 | 84 | 93 |
| 8 | 3-tert . butylphenol | 2-hydroxy-4-tert . butylbenzaldehyde | 84 | 72 | 85 |
| 9 | 3-chlorophenol | 2-hydroxy-4-chlorobenzaldehyde(+) 2-hydroxy-6-chlorobenzaldehyde | 60 | 55(+) | 92 |
| 10 | 2-phenylphenol | 2-hydroxy-3-phenylbenzaldehyde | 65 | 60 | 92 |
| 11 | 4-methoxyphenol | 2-hydroxy-5-methoxybenzaldehyde | 55 | 45 | 82 |
| 12 | 2-nonylphenol | 2-hydroxy-3-nonyl-benzaldehyde | 75 | 65 | 86 |
| 13 | hydroquinone | 2,5-dihydroxybenzaldehyde | 54 | 48 | 88 |
| 14 | 3-acetylaminophenol(++) | 2-hydroxy-4-acetylaminobenzaldehyde | 75 | 50 | 66 |

(+)75% of 4-chloro, 25% of 6-chloro derivative
(++)solvent: anisole

TABLE II

Syntheses of 2-hydroxy-3-methylbenzaldehyde from ortho-cresol (0.1 mole) and paraformaldehyde in the presence of $SnCl_2$ (0.01 mole) and 4-methylpyridine (0.04 mole) in toluene (200 cc) under different operating conditions, for 8 hours.

| Example | T. °C. | PhOH/CH$_2$O | Conv. % | Yield % | Select. % |
|---|---|---|---|---|---|
| 15 a | 90 | ⅓ | 70 | 67 | 95 |
| 15 b | 150 | ⅓ | 100 | 70 | 70 |
| 15 c | 110 | ⅓ | 75 | 70 | 93 |
| 2 a | 110 | ⅓ | 90 | 85 | 94 |

TABLE III

Syntheses of 2-hydroxy-3-methylbenzaldehye from ortho-cresol (0.1 mol) and paraformaldehye (0.3 mole) in the presence of $SnCl_2$ and 4-methylpyridine in toluene (200 cc) at 110° C. for 8 hours.

| Example | PhOH SnCl$_2$ | PhOH 4-methylpyridine | Conv. % | Yield % | Select. % |
|---|---|---|---|---|---|
| 16 a | 1/0.2 | 1/0.4 | 91 | 83 | 91 |
| 16 b | 1/0.02 | 1/0.4 | 60 | 57 | 95 |
| 16 c | 1/0.1 | 1/0.1 | 90 | 81 | 90 |
| 16 d | 1/0.1 | 1/0.6 | 88 | 83 | 94 |

TABLE IV

Syntheses of 2-hydroxy-3-methylbenzaldehyde from ortho-cresol (0.1 mole) and paraformaldehyde (0.3 mole) in the presence of $SnCl_2$ (0.01 mole) and various binders (0.04 mole) in toluene (200 cc) at 110° C. for 8 hours.

| Example | Binder | Conv. % | Yield % | Select. % |
|---|---|---|---|---|
| 17 a | pyridine | 90 | 83 | 92 |
| 17 b | 2,4-dimethylpyridine | 87 | 83 | 95 |
| 17 c | 4-acetylpyridine | 91 | 84 | 92 |
| 17 d | N,N,N',N'-tetramethylethylene diamine | 93 | 86 | 92 |
| 17 e | hexamethylenephosphotriamide | 93 | 84 | 90 |
| 17 f | 4-ethylpyridine | 86 | 83 | 96 |
| 17 g | N,N,N',N'-tetramethylpropylene diamine | 91 | 84 | 92 |

Syntheses of 2-hydroxy-3-methylbenzaldehyde from ortho-cresol (0.1 mole) and paraformaldehyde under general conditions different from those of the present process, conducted in 8-hour periods and in 200

TABLE IV-continued

| Ex. | T° C. | Catalyst | Binder | Solvent | cc of solvent. PhOH CH₂O | PhOH Catal. | PhOH Binder | Conv. % | Yield % | Selec. % |
|---|---|---|---|---|---|---|---|---|---|---|
| 18a | 80 | SnCl₂ | 4-picoline | toluene | 1/3 | 1/0.1 | 1/0.1 | 36 | 34 | 94 |
| 18b | 160 | SnCl₂ | 4-picoline | toluene | 1/3 | 1/0.1 | 1/0.4 | 100 | 36 | 36 |
| 18c | 110 | — | 4-picoline | toluene | 1/3 | — | 1/0.4 | 14 | 0 | 0 |
| 18d | 110 | ZnCl₃ | 4-picoline | toluene | 1/3 | 1/0.1 | 1/0.4 | 74 | 8 | 11 |
| 18e | 110 | MgCl₂ | 4-picoline | toluene | 1/3 | 1/0.1 | 1/0.4 | 77 | 7 | 9 |
| 18f | 110 | AlCl₃ | 4-picoline | toluene | 1/3 | 1/0.1 | 1/0.4 | 70 | 0 | 0 |
| 18g | 110 | CuBr₂ | 4-picoline | toluene | 1/3 | 1/0.1 | 1/0.4 | 46 | 0 | 0 |
| 18h | 110 | SnCl₂ | — | toluene | 1/3 | 1/0.1 | — | 67 | 0 | 0 |
| 18i | 110 | SnCl₂ | diglyme | toluene | 1/3 | 1/0.1 | 1/0.4 | 65 | 0 | 0 |
| 18j | 110 | SnCl₂ | butylphosphite | toluene | 1/3 | 1/0.1 | 1/0.4 | 43 | 0 | 0 |
| 18k | 110 | SnCl₂ | butanol | toluene | 1/3 | 1/0.1 | 1/0.4 | 24 | 0 | 0 |
| 18l | 110 | SnCl₂ | 4-picoline | H₂O | 1/3 | 1/0.1 | 1/0.4 | 72 | 0 | 0 |
| 18m | 110 | SnCl₂ | 4-picoline | diglyme | 1/3 | 1/0.1 | 1/0.4 | 13 | 3 | 23 |
| 18n | 110 | SnCl₂ | 4-picoline | DMSO | 1/3 | 1/0.1 | 1/0.4 | 12 | 4 | 30 |
| 18o | 110 | SnCl₂ | 4-picoline | toluene | 1/1 | 1/0.1 | 1/0.4 | 38 | 15 | 39 |
| 18p | 110 | SnCl₂ | 4-picoline | toluene | 1/3 | 1/0.01 | 1/0.4 | 27 | 18 | 66 |
| 18q | 110 | SnCl₂ | 4-picoline | toluene | 1/3 | 1/0.1 | 1.0.01 | 80 | 23 | 28 | diglyme = dimethylether of diethylene glycol
DMSO = dimethylsulphoxide

The salicyclic aldehyde and its derivatives prepared by the present process are used, for example, in perfumes, as fungicides and larvacides and as stabilizing agents for polystyrene resins. In addition, these aldehydes are intermediates for the synthesis of various useful products, for example in the preparation of coumarins, hydroxyamines, benzopyrans, various heterocycles, etc. Some of such products, (e.g., semicarbazones, Schiff bases, oximes, etc.,) are used as stabilizers for formaldehyde polymers, for benzines, for PVC and other thermoplastic resins and, also, as insecticides, anti-microbial agents and cationic complexing agents.

What we claim is:

1. Process for preparing 2-hydroxy-benzoic aldehydes having the general formula (I):

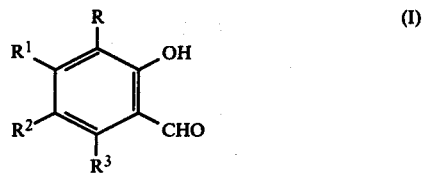
(I)

wherein R, R¹, R² and R³, which can be the same or different, represent hydrogen atoms; alkyl, aryl, cycloalkyl, alkoxyl, hydroxyl, or acylamino groups, or halogen; characterized in that a phenol of general formula (II)

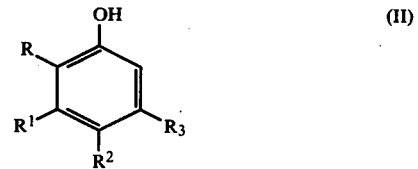
(II)

wherein R, R¹, R² and R³ have the same meaning as in general formula (I), is condensed with formaldehyde at temperatures of from about 90° to 150° C., in a substantially stoichiometric molar ratio between phenol (II) and formaldehyde, in the presence of anhydrous stannous and/or stannic chloride, in ratios comprised between about 0.02 and 0.2 mole expressed as Sn for one mole of phenol (II), and of a binder selected from the group consisting of pyridine, alkylpyridines, acetylpyridines, hexamethylphosphotriamide, tetramethylethylenediamine, tetramethylpropylenediamine, quinolines, quinoxalines, anilines, substituted anilines and tertiary amines, in an aprotic solvent.

2. The process of claim 1, in which the condensation reaction is carried out at a temperature of about 110° C.

3. The process of claim 1, in which the phenol of general formula (II) is condensed with paraformaldehyde.

4. The process of claim 1, in which about 0.1 mole of catalyst, expressed as Sn, is used per mole of the phenol (II).

5. The process of claim 1, in which the binder is used in a molar ratio of from about 0.1 to 0.6 mole, per mole of the phenol (II).

6. The process of claim 5, in which the binder is used in an amount of about 0.4 mole per mole of the phenol (II).

7. The process of claim 1, in which the aprotic solvent is at least one compound selected from the group consisting of toluene, xylenes, cumene, alkylbenzenes, decalin and anisole.

8. The process of claim 1, in which the catalyst is anhydrous SnCl₂.

* * * * *